(12) United States Patent
Leahy et al.

(10) Patent No.: US 9,752,402 B2
(45) Date of Patent: Sep. 5, 2017

(54) DRILL SAMPLE PARTICLE DISTRIBUTOR

(71) Applicant: METZKE PTY LTD, Canning Vale (AU)

(72) Inventors: Matthew K. Leahy, Canning Vale (AU); Tomas Borg, Canning Vale (AU)

(73) Assignee: METZKE PTY LTD, Canning Vale (AU)

( * ) Notice: Subject to any disclaimer, the term of this patent is extended or adjusted under 35 U.S.C. 154(b) by 209 days.

(21) Appl. No.: 14/647,287

(22) PCT Filed: Dec. 20, 2013

(86) PCT No.: PCT/AU2013/001513
§ 371 (c)(1),
(2) Date: May 26, 2015

(87) PCT Pub. No.: WO2014/110619
PCT Pub. Date: Jul. 24, 2014

(65) Prior Publication Data
US 2015/0300116 A1 Oct. 22, 2015

(30) Foreign Application Priority Data

Jan. 21, 2013 (AU) ................................ 2013900236

(51) Int. Cl.
*E21B 49/00* (2006.01)
*E21B 25/00* (2006.01)
(Continued)

(52) U.S. Cl.
CPC .............. *E21B 25/005* (2013.01); *B05B 3/02* (2013.01); *B05B 3/14* (2013.01); *E21B 49/005* (2013.01);
(Continued)

(58) Field of Classification Search
CPC ...... E21B 25/005; E21B 49/005; E21B 49/02; B05B 1/02; B05B 1/14; G01N 11/08; G01N 11/2211
(Continued)

(56) References Cited

U.S. PATENT DOCUMENTS 3,563,255 A * 2/1971 Morris .................... B01D 35/20
134/133
3,565,342 A * 2/1971 Orem ........................ B05B 3/02
239/227

(Continued)

FOREIGN PATENT DOCUMENTS

| DE | 26 28 651 | 9/1977 |
|---|---|---|
| JP | 05-184994 | 7/1993 |

OTHER PUBLICATIONS

Gerlach, et al., "Gy sampling theory in environmental studies. 1. Assessing soil splitting protocols", Journal of Chemometrics, vol. 16, No. 7, Jul. 1, 2002, pp. 321-328.
(Continued)

*Primary Examiner* — Arthur O Hall
*Assistant Examiner* — Viet Le
(74) *Attorney, Agent, or Firm* — Hamre, Schumann, Mueller & Larson, P.C.

(57) ABSTRACT

A particle distributor assembly 10 for distributing the particles of a drill sample is described. The distributor assembly comprises a stationary inlet tube 14 through which particles enter the distributor assembly 10, and a rotatable distributor head 16. The rotatable distributor head 16 has an upwardly directed inlet 18 offset from a central axis of rotation of the distributor head 16 and a transversely directed outlet 22 wherein, in use, when the distributor head 16 is rotated at high speed particles entering the distributor head inlet are accelerated outwardly in a radial direction through the distributor head outlet. The particle distributor assembly 10
(Continued)

also has a distributor nozzle 24 having an inlet 26 and an outlet 28, the nozzle inlet 26 being aligned with the stationary inlet tube and the nozzle outlet 28 being aligned with the distributor head inlet. The distributor nozzle 24 is supported between the inlet tube 14 and the distributor head 16 in such a manner that it is constrained from rotating while the nozzle outlet 28 is able to oscillate in a circular motion with the distributor head inlet 18. In use, the oscillating motion of the nozzle outlet 28 helps to promote particle flow and produce a more representative distribution of particles exiting from the distributor head outlet 22.

11 Claims, 3 Drawing Sheets

(51) Int. Cl.
*B05B 3/02* (2006.01)
*B05B 3/14* (2006.01)
*E21B 49/02* (2006.01)
*G01N 1/08* (2006.01)
*G01N 1/22* (2006.01)

(52) U.S. Cl.
CPC ............... *E21B 49/02* (2013.01); *G01N 1/08* (2013.01); *G01N 1/2211* (2013.01)

(58) Field of Classification Search
USPC .......................................................... 239/227
See application file for complete search history.

(56) References Cited

U.S. PATENT DOCUMENTS

| | | | | | |
|---|---|---|---|---|---|
| 3,576,262 | A | * | 4/1971 | Konchesky | B65G 69/00 193/3 |
| 3,799,445 | A | * | 3/1974 | Marino | B05B 3/14 118/317 |
| 3,871,486 | A | * | 3/1975 | Curington | E21B 4/14 175/100 |
| 3,883,073 | A | * | 5/1975 | Ballu | A01M 7/006 239/227 |
| 3,887,020 | A | * | 6/1975 | Chaffin | E21B 21/00 175/206 |
| 3,968,845 | A | * | 7/1976 | Chaffin | E21B 21/00 175/206 |
| 4,106,161 | A | * | 8/1978 | Niccolls | A22C 21/0061 452/106 |
| 4,272,020 | A | * | 6/1981 | Allison | B05B 3/02 239/10 |
| 4,369,850 | A | * | 1/1983 | Barker | B05B 3/02 175/393 |
| 4,530,462 | A | * | 7/1985 | Andersson | A01C 15/04 239/222.17 |
| 5,637,357 | A | * | 6/1997 | Stachelhaus | B05B 5/032 118/622 |
| 6,402,048 | B1 | * | 6/2002 | Collins | B05B 3/02 239/210 |
| 2007/0207485 | A1 | * | 9/2007 | Deppermann | G01N 1/04 435/6.12 |
| 2008/0105062 | A1 | * | 5/2008 | Lennox Day | E21B 49/00 73/863 |
| 2009/0136660 | A1 | * | 5/2009 | Brune | D04H 3/05 427/180 |
| 2012/0118994 | A1 | * | 5/2012 | Drechsel | A01G 25/092 239/230 |
| 2015/0223596 | A1 | * | 8/2015 | Topf | A46B 13/04 427/429 |
| 2015/0300116 | A1 | * | 10/2015 | Leahy | E21B 49/02 239/227 |
| 2016/0199679 | A1 | * | 7/2016 | Kusu | A62C 31/05 239/243 |
| 2016/0290131 | A1 | * | 10/2016 | Mitchell | E21B 47/102 |
| 2016/0356679 | A1 | * | 12/2016 | Zhang | G01N 1/24 |
| 2016/0368799 | A1 | * | 12/2016 | Tabata | C02F 3/043 |
| 2017/0016856 | A1 | * | 1/2017 | Zhang | G01N 1/02 |
| 2017/0072421 | A1 | * | 3/2017 | Baumann | B05B 3/02 |

OTHER PUBLICATIONS

Extended European Search Report issued in corresponding European Patent Application No. 13871588.3, Oct. 10, 2016, 8 pages.
International Search Report and Written Opinion of International PCT application No. PCT/AU2013/001513, dated Mar. 20, 2014, 8 pages.

* cited by examiner

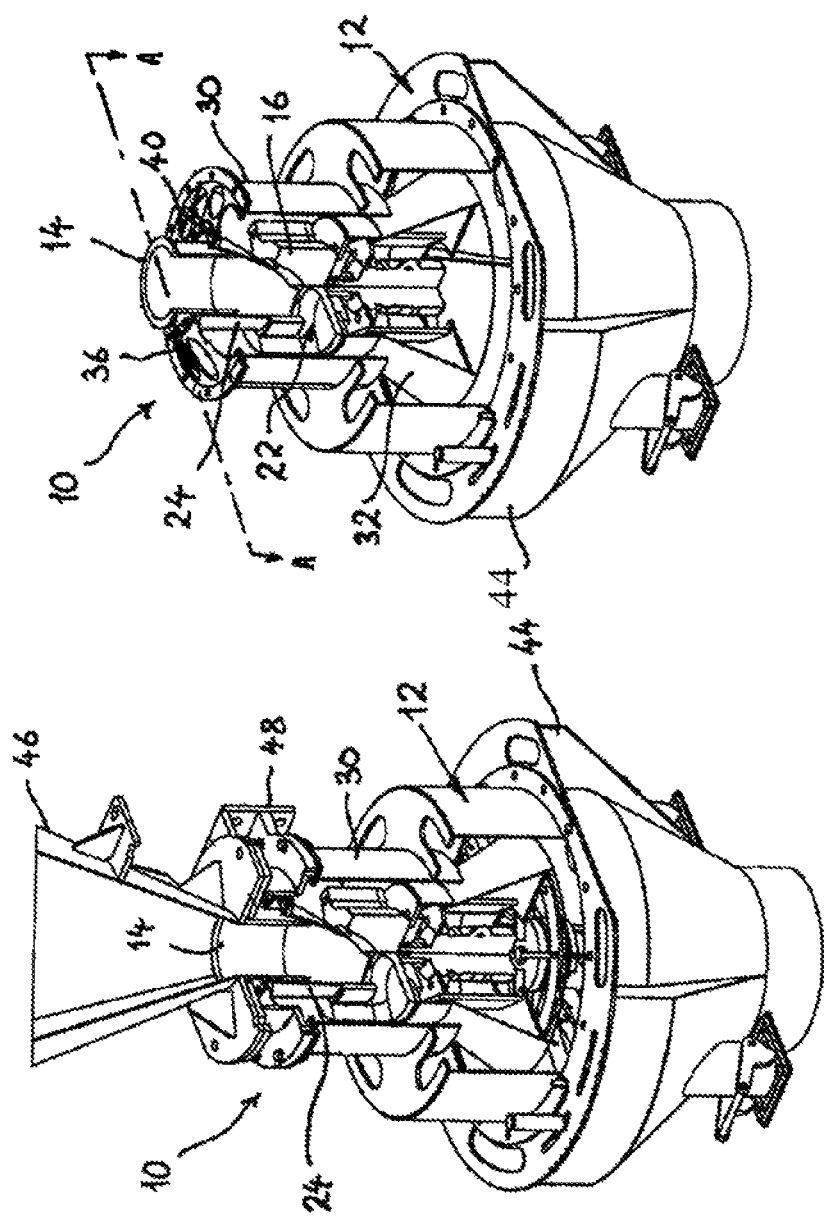

DRILL SAMPLE PARTICLE DISTRIBUTOR

FIELD OF THE INVENTION

The present invention relates to a drill sample particle distributor for more uniformly distributing the particles of a drill sample and relates particularly, although not exclusively, to such a particle distributor for more uniformly distributing the particles of a drill sample at the inlet of a cone splitter.

BACKGROUND TO THE INVENTION

The search for minerals beneath the earth's surface often requires physical "samples" of the rock to be taken. Drill rigs are used to drill holes and retrieve the drilled material from the hole. This material is called a "drill sample". The reverse circulation (RC) method of drilling is commonly used to drill and retrieve the sample, because it is relatively fast and produces good quality samples. RC uses large volumes of high pressure air to power the downhole drilling tool; the exhaust air then conveys the sample to the surface through inner tubes located within the drill rods. The sample then continues through a large hose to the drill sampling system.

Most drill sampling systems consist of a cyclone to slow down and separate the cuttings from the airstream, a drop box to collect the sample, and a sample splitter. A sample splitter is a device that is designed to consistently and accurately divide a bulk quantity of material into smaller portions that are truly representative of the bulk. In the case of drill sampling, it is usual to "split" the bulk material from a drilled interval into one or two small "laboratory samples" and the remainder as "waste". The small samples are generally known as the 'assay' and 'duplicate' samples. These samples are usually required to be a consistent percentage (normally between 5 and 10%) of the bulk material and both of the same size.

There are various types of splitter used, but there is a tendency now toward "cone" splitters as being more accurate in this application. The cone splitter consists of a cone oriented with the point up. This would be enclosed in a body with an inlet or funnel at the top which is centrally located over, and just above, the point of the cone. Under the lower edge of the cone are one or more radial "cutters" or chutes. The bulk material to be split falls through the inlet, over the point of the cone, and then flows in an even spread down the slope of the cone. The cutters or chutes under the lower edge of the cone will catch a portion of the bulk material and direct it away to be collected as the assay and/or duplicate. The remainder or 'waste' is usually directed into a bulk bag or wheelbarrow.

For a cone splitter to split correctly the sample must be distributed evenly around the circumference of the base of the cone where the cutters/chutes are. The cutters/chutes must also be of a correct segment shape and have knife 'cutting' edges. It follows that for an even distribution at the bottom of the cone, there must be an even or uniform distribution over the point of the cone. The cone must also be level and evenly formed. So for a cone splitter to work correctly, the bulk material must be distributed uniformly onto the point of the cone. To spread evenly over the cone the cuttings must be dropped through a circular inlet, positioned centrally over the point of the cone.

Ideally this inlet should be as small as possible to produce a slow and consistent flow and to funnel the cuttings over the cone (like an hour glass). When drilling dry material, the cuttings are slowed by the cyclone and collected in the drop box. Usually the complete interval is collected before being dropped as one onto the splitter. This fills the inlet, and the cuttings generally flow quite consistently onto the cone, producing an even spread and hence an accurate split.

An inlet that is too small will tend to block because of varying particle size and moisture content of the cuttings. Time taken to process each sample also becomes too long. These factors have dictated that the minimum practical inlet size for dry cuttings is approximately 120 mm. If water is encountered in the drilling process, or if water needs to be injected into the drilling air, the sample then becomes wet. When wet drilling, there often are huge rapid variations in the flow rate of cuttings into the cyclone. This is due to changing water flow rates in the formation, and also the dynamics of using compressed air to power downhole hammers and lift the cuttings. Flow can vary from little or nothing for the majority of the drilled interval, to a large rush of cuttings at the end of the interval when the hammer is 'lifted off bottom'. Even with average water flows, the volume of sample and water can often exceed the capacity of the drop box. For this reason the drop box door usually has to remain open, allowing the cuttings to flow directly from the cyclone, through the drop box, and into the splitter.

This changing flow rate produces uncontrolled streams into the splitter that often favour or bias one side of the cone. This bias can produce large variations in sample size and accuracy. For example, if all the flow is down one side of the cone, directly above a cutter, then there will be a vastly oversize sample from that cutter, whilst the other cutter may well produce an undersize sample. Wet sample will flow through a much smaller hole, but again variations in flow rates and changes from dry/wet/dry sampling make it impractical to reduce inlet size.

Rotating type cone splitters have been developed to try and counteract this bias. These either rotate the cone and cutters and redirect the sample through a convoluted system of funnels and chutes to the collection bags, or they rotate the entire collection system under the cone. Rotary cone splitters assume that there is a biased flow over the cone, and attempt to pass the cutters through that flow wherever that flow may be around the base of the cone. Doing this many times per sample interval should produce a reasonably representative sample, but in practice this does not always happen.

Accepted sampling practice dictates cutter speed through the sample stream to be no more than 500 mm/sec, which translates to only about 20-25 rpm for current size cone splitters. Current rotary type cone splitters or rotary distributors on the market rotate at about than 50-60 rpm, which is beyond accepted speeds and introduces delimitation errors with the sample.

In wet drilling of a softer formation it often occurs that almost the entire sample comes into the system within a few seconds as the hammer is 'lifted off bottom' at the end of the interval. This is a normal result during drilling and little can be done to modify it. As there is currently no way of throttling the flow of wet sample and distributing it over the cone, it often occurs that the entire sample can pass over the cone within a few seconds. This flow is also often heavily biased to one or more areas of the cone. Even at the higher than recommended rotating speeds, the rotating cutters or collectors are only passing any given part of the cone at a rate of no more than once per second each, so they may only take a few small increments of the entire sample.

A drilled sample generally comes into the splitter in the order or sequence that it is drilled, and hence falls over the splitter in the same sequence that it occurs in situ. If the formation being drilled is very stratified, then it is probable that much of the interval will effectively not be sampled, as there will only be a few increments taken. So it is accepted that the flow of wet sample over a cone is often biased and therefore produces inconsistent and biased samples. Corrections need to be made to produce a more representative sample.

Prior art attempts to address this problem have done so in several ways:

1. Rotate the collection points beneath a stationary cone; or
2. Rotate the cone and sample cutters, and direct the sample to fixed collection funnels.
3. Channel the sample to the cutters through a rotating chute or funnel (as with the Progradex "Andis" sampler).

From a theoretical sampling point of view, rotating cutters, whilst not perfect are a fairly accurate way to take a representative sample, but this also assumes a relatively homogeneous sample stream and a relatively steady and slow flow rate. Neither of these occurs reliably in practice. All the above methods take an increment of sample each revolution, but as described above, there can often be only a few increments taken throughout each interval. This is due to physical limitations on the rotation speed of the funnel, the cone or the cutters and sample extraction errors incurred with higher cutter speed. At higher rotational speeds, centrifugal forces also begin to have a major detrimental effect on the flow and distribution of the sample.

Until now there has been little or no control over the way the cuttings are distributed as they enter the splitter. The present invention was developed with a view to providing a drill sample distributor for more uniformly distributing the particles of a drill sample at the inlet of a cone splitter. This means that a stationary cone can be used and there are none of the inherent constraints and limitations of prior rotary cone splitters or distributors. However it will be appreciated that the particle distributor may have other applications where particles are required to be distributed more uniformly.

References to prior art documents in this specification are provided for illustrative purposes only and are not to be taken as an admission that such prior art is part of the common general knowledge in Australia or elsewhere.

SUMMARY OF THE INVENTION

According to one aspect of the present invention there is provided a particle distributor assembly for distributing the particles of a drill sample, the distributor assembly comprising:
a stationary inlet tube through which particles enter the distributor assembly;
a rotatable distributor head having an upwardly directed inlet offset from a central axis of rotation of the distributor head and a transversely directed outlet wherein, in use, when the distributor head is rotated at high speed particles entering the distributor head inlet are accelerated outwardly in a radial direction through the distributor head outlet; and,
a distributor nozzle having an inlet and an outlet, the nozzle inlet being aligned with the stationary inlet tube and the nozzle outlet being aligned with the distributor head inlet, the distributor nozzle being supported between the inlet tube and the distributor head in such a manner that it is constrained from rotating whilst the nozzle outlet is forced to oscillate in a circular pattern by the rotation of the distributor head inlet whereby, in use, the oscillating motion of the nozzle outlet helps to promote particle flow and produce a more representative distribution of particles exiting from the distributor head outlet.

Preferably the distributor nozzle is supported between the inlet tube and the distributor head by a flexible support member. In one embodiment the flexible support member is in the form of an annular plate of flexible, resilient material. Preferably an outer circumference of the plate is mounted on a housing of the distributor assembly and an inner circumference of the plate is fixed to the nozzle inlet. In this embodiment the inner circumference of the plate is fixed to the nozzle inlet by a retaining ring. In another embodiment the flexible support member and distributor nozzle are manufactured as a single integrated component.

Preferably the distributor assembly further comprises an annular skirt surrounding the rotatable distributor head and adapted to redirect the particles exiting from the distributor head outlet in a downwards direction. In one embodiment the skirt is provided by a cylindrical housing wall of the distributor assembly.

Typically the rotatable distributor head is driven by a drive motor. In one embodiment the drive motor comprises a hydraulic motor. Advantageously the distributor head and the oscillating distributor nozzle are balanced and rotation speeds of between 50 to 500 rpm are achievable with near perfect sample distribution from the distributor head outlet and with no material hang-up.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of a specific embodiment of the drill sample distributor, given by way of example only, with reference to the accompanying drawings, in which:

FIG. 1 is top perspective, partially cut-away view of a first embodiment a drill sample particle distributor according to the invention;

FIG. 2 is a top perspective, partially cut-away view of the drill sample particle distributor, similar to FIG. 1 except that the top material feed cone has been removed for clarity;

DETAILED DESCRIPTION OF PREFERRED EMBODIMENTS

Figure 3:
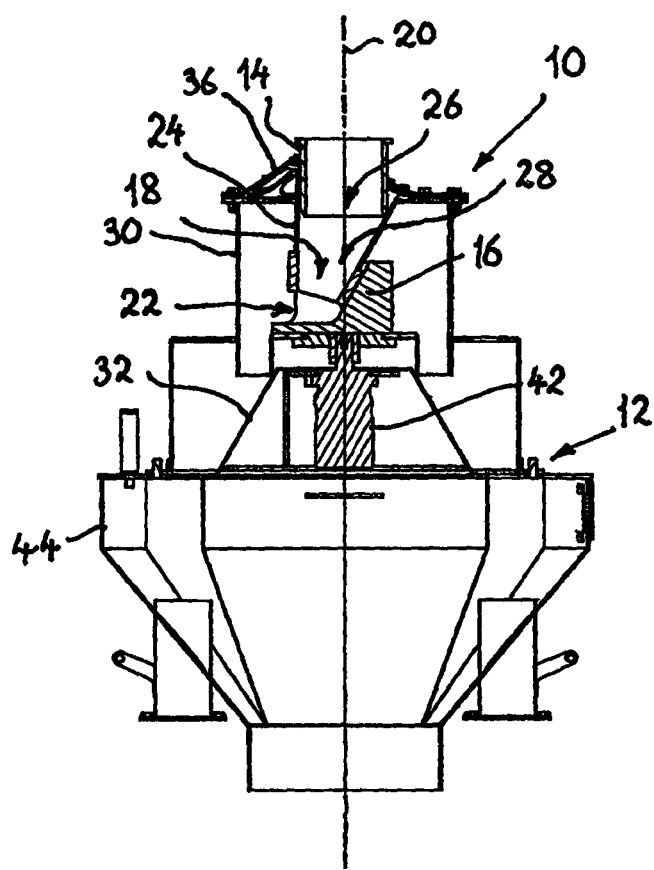
FIG. 3 is a section view of the drill sample particle distributor through the lie A-A as shown in FIG. 2; and, FIG. 4 is an enlarged top perspective, partially cut-away view of the drill sample particle distributor similar to that of FIG. 2.
Figure 4:
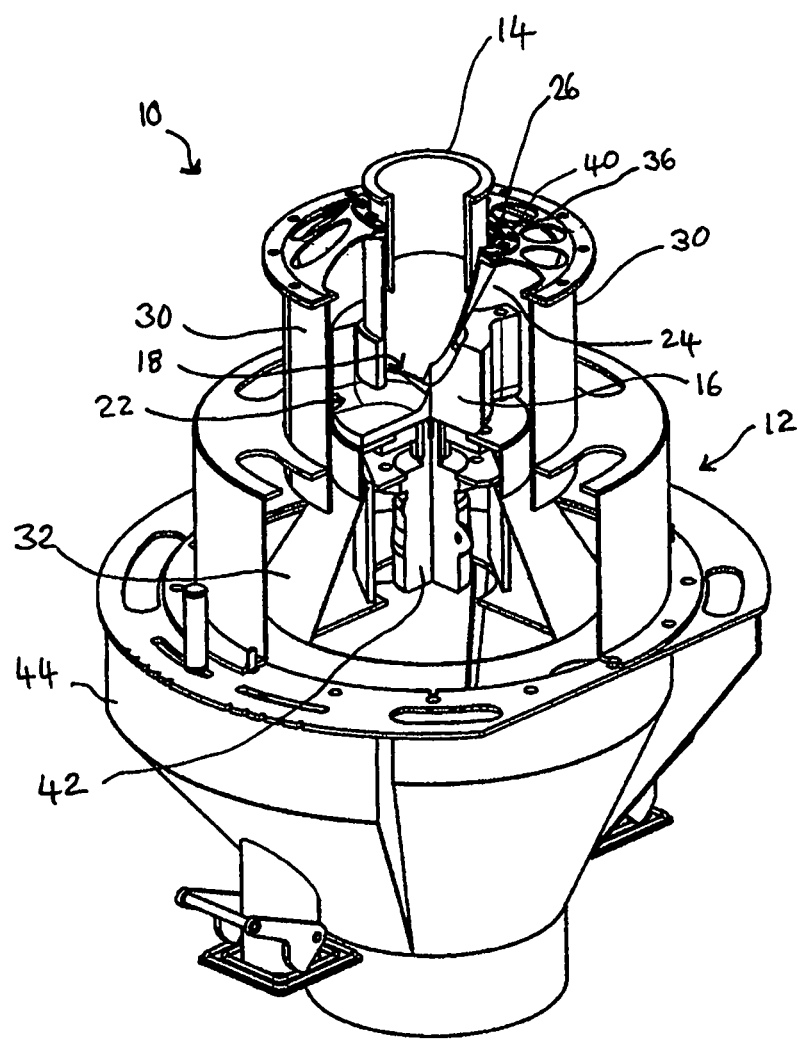

A preferred embodiment of a particle distributor assembly 10 for distributing the particles of a drill sample at the inlet of a cone splitter 12, as illustrated in FIGS. 1 to 4, comprises a stationary inlet tube 14 through which drill sample particles enter the distributor assembly 10. A rotatable distributor head 16 is provided, having an upwardly directed inlet 18 offset from a central axis of rotation 20 (see FIG. 3) of the distributor head 16. A transversely directed outlet 22 is in direct fluid communication with the distributor head inlet 18 wherein, in use, when the distributor head 16 is rotated at high speed particles entering the distributor head inlet 18 are accelerated outwardly in a radial direction through the distributor head outlet 22.

The sample particle distributor assembly 10 further comprise a distributor nozzle 24 having an inlet 26 and an outlet 28. The nozzle inlet 26 is aligned with the stationary inlet tube 14 and the nozzle outlet 28 is aligned with the distributor head inlet 18, the distributor nozzle 24 being supported between the inlet tube 14 and the distributor head 16 in such a manner that it is constrained from rotating. At the same time the nozzle outlet 28 is able to oscillate in a circular motion with the distributor head inlet 18 whereby, in use, the oscillating motion of the nozzle outlet 28 helps to promote particle flow and produce a more representative distribution of sample particles exiting from the distributor head outlet 22.

Preferably the distributor assembly 10 further comprises a stationary annular skirt 30 surrounding the rotatable distributor head and adapted to redirect the sample particles exiting from the distributor head outlet in a downwards direction.

In view of the problems with the prior art noted above, it was realised that to provide a more representative distribution of sample particles over a cone splitter with inconsistent feed material flows, a much greater rotational speed of the distributor or cone is required. However, as noted above, high rotational speeds of cutters or cones through a sample stream lead to delimitation error and also balance and safety issues due to rotating mass.

It was recognised that by spreading the sample radially against an inner wall of the skirt 30 it would be possible to rotate the distributor head 16 at high speed while using the skirt 30 to redirect the sample particles downwards to fall over a stationary cone 32 of the cone splitter 12 in the traditional manner. The sample particles then have little or no radial or rotational motion as they fall over the cone 32.

Initial attempts to distribute sample particles via a rotating head with the inlet of the head concentric with the centre of rotation at speeds greater than about 50 rpm, led to major problems with material hang-up and reduced flow in the head. As the centre of rotation of the head is also the centre of the inlet tube, up to 50% of the head wall will impart a centrifugal force on any contained material away from the distributor head outlet direction. As rotational speed increases, that material then will not exit the distributor head outlet and consequently blocks the entire distributor assembly.

However by locating the distributor head inlet 18 offset from the central axis of rotation of the distributor head 16 and the inlet tube 14, these problems can be substantially eliminated. The oscillating motion of the nozzle outlet 28 imparts no centrifugal forces to the sample particles whilst in the distributor nozzle 24, and in fact particles flowing through the distributor nozzle 24 experience a violent horizontal action at any point in the distributor nozzle which helps promote sample flow and virtually eliminates hang up.

The sample particles flow through the nozzle outlet 28 into the inlet 18 of rotating distributor head 16, where the entire sample portion is now on one side (the outlet side) of the central axis of rotation 20 and is consequently accelerated out in a radial direction through the distributor head outlet 22 to impact the skirt 30 and subsequently fall over the cone 32. In the illustrated embodiment the skirt is provided by a cylindrical housing wall 30 of the distributor assembly 10, as can be seen most clearly in FIGS. 3 and 4. However the skirt 30 may also be manufactured or moulded as a separate item to provide better flow and/or wear characteristics.

Preferably the distributor nozzle 24 is supported between the inlet tube 26 and the distributor head 16 by a flexible support member 36. In the illustrated embodiment the flexible support member is in the form of an annular plate 36 made of flexible, resilient material, for example, rubber. The distributor nozzle 24 is suspended by and restrained from rotating by the annular plate 36, as the nozzle outlet 28 is forced to oscillate in a circular pattern by the rotation of the distributor head 16. In use, the plate 36 wobbles and stretches to accommodate the oscillating motion of the distributor nozzle 24. The wobbly plate 36 of this embodiment is formed with a series of holes at spaced intervals about its circumference to further facilitate the wobbling and stretching of the rubber.

An outer circumference of the wobbly plate 36 is mounted on the housing wall 30 of the distributor assembly 10, and an inner circumference of the wobbly plate 36 is fixed to the nozzle inlet 26. In this embodiment the inner circumference of the plate is fixed to the nozzle inlet by a retaining ring 40, as can be seen most clearly in FIGS. 2 and 4. In another embodiment the flexible support member 36, retaining ring 40 and distributor nozzle 24 may be manufactured as a single integrated component.

Both the distributor head 16 and the oscillating distributor nozzle 24 are balanced and rotation speeds up to 500 rpm are now achievable with near perfect sample distribution over the cone 32 and with no material hang-up. In this embodiment, the rotatable distributor head 16 is driven by a hydraulic motor 42 that is fixed to the lower cone splitter assembly 44. However it will be appreciated that any suitable drive motor may be used to drive the distributor head.

The sample material is fed into the distributor assembly 10 via a feed chute 46 which directs the sample particles into the inlet tube 14. A connecting flange 48 is provided between the material feed chute 46 and the distributor assembly 10. The connecting flange 48 also serves to retain the inlet tube 14, and clamps the outer circumference of the wobbly plate 36 to an annular flange on the upper edge of the housing wall 30, as can be seen in FIG. 1. In this manner the distributor assembly 10 can be fully integrated with the cone splitter 12 to form a single compact unit.

On the other hand, the distributor assembly 10 may not necessarily need to feed to a cone splitter (as it does in this embodiment), but may be used to distribute sample particles directly to sample cutters or collectors. As the sample is distributed evenly against the skirt 30 and falls evenly from the skirt there may not be a need for the cone 32. This would simplify and shorten the overall length of the assembly.

Now that a preferred embodiment of the drill sample particle distributor has been described in detail, it will be apparent that the embodiment provides a number of advantages, including the following:

(i) It provides an effective means of providing a more representative distribution of particles of a drill sample at the inlet of a cone splitter.

(ii) The non-rotating distributor nozzle distributes the sample particles without material hang-up by allowing the nozzle outlet to oscillate in a circular pattern over the cone splitter.

(iii) It allows a stationary cone to be used which avoids the inherent constraints and limitations of rotary cone splitters.

(iv) It is simple to operate and can be retrofitted to existing splitters.

It will be readily apparent to persons skilled in the relevant arts that various modifications and improvements may be made to the foregoing embodiments, in addition to those already described, without departing from the basic inventive concepts of the present invention. For example, the manner of supporting the distributor nozzle to prevent it from rotating whilst permitting the nozzle outlet to oscillate in a circular motion may vary considerably from that shown. The wobbly plate provides an effective way to do this; however it will be appreciated that other mechanical arrangements may also suffice. Therefore, it will be appreciated that the scope of the invention is not limited to the specific embodiments described.

The invention claimed is:

1. A particle distributor assembly for distributing the particles of a drill sample, the distributor assembly comprising:
    a stationary inlet tube through which particles enter the distributor assembly;
    a rotatable distributor head having an upwardly directed inlet offset from a central axis of rotation of the distributor head and a transversely directed outlet wherein, in use, when the distributor head is rotated at high speed particles entering the distributor head inlet are accelerated outwardly in a radial direction through the distributor head outlet; and,
    a distributor nozzle having an inlet and an outlet, the nozzle inlet being aligned with the stationary inlet tube and the nozzle outlet being aligned with the distributor head inlet, the distributor nozzle being supported between the inlet tube and the distributor head in such a manner that it is constrained from rotating whilst the nozzle outlet is forced to oscillate in a circular pattern by the rotation of the distributor head inlet whereby, in use, the oscillating motion of the nozzle outlet helps to promote particle flow and produce a more representative distribution of particles exiting from the distributor head outlet.

2. A particle distributor assembly as defined in claim 1, wherein the distributor nozzle is supported between the inlet tube and the distributor head by a flexible support member.

3. A particle distributor assembly as defined in claim 2, wherein the flexible support member is in the form of an annular plate of flexible, resilient material.

4. A particle distributor assembly as defined in claim 3, wherein an outer circumference of the plate is mounted on a housing of the distributor assembly and an inner circumference of the plate is fixed to the nozzle inlet.

5. A particle distributor assembly as defined in claim 4, wherein the inner circumference of the plate is fixed to the nozzle inlet by a retaining ring.

6. A particle distributor assembly as defined in claim 2, wherein the flexible support member and distributor nozzle are manufactured as a single integrated component.

7. A particle distributor assembly as defined in claim 1, wherein the distributor assembly further comprises an annular skirt surrounding the rotatable distributor head and adapted to redirect the particles exiting from the distributor head outlet in a downwards direction.

8. A particle distributor assembly as defined in claim 7, wherein the skirt is provided by a cylindrical housing wall of the distributor assembly.

9. A particle distributor assembly as defined in claim 1, wherein the rotatable distributor head is driven by a drive motor.

10. A particle distributor assembly as defined in claim 9, wherein the drive motor comprises a hydraulic motor.

11. A particle distributor assembly as defined in claim 1, wherein the distributor head and the oscillating distributor nozzle are balanced and rotation speeds of between 50 to 500 rpm are achievable with near perfect sample distribution from the distributor head outlet and with no material hang-up.

* * * * *